United States Patent [19]

Yehuda

[11] Patent Number: 4,851,431

[45] Date of Patent: Jul. 25, 1989

[54] PHYSIOLOGICALLY ACTIVE AND NUTRITIONAL COMPOSITION

[75] Inventor: Shlomo Yehuda, Tel Aviv, Israel

[73] Assignee: Bar Ilan University, Israel

[21] Appl. No.: 120,830

[22] Filed: Nov. 16, 1987

[30] Foreign Application Priority Data

Nov. 26, 1986 [IL] Israel .................................. 80786
Oct. 25, 1987 [IL] Israel .................................. 84273

[51] Int. Cl.$^4$ ............................................. A01N 37/00
[52] U.S. Cl. .................................... 514/560; 424/439; 424/440
[58] Field of Search ................ 514/560; 424/439, 440

[56] References Cited

U.S. PATENT DOCUMENTS

| | | |
|---|---|---|
| Re. 31,836 | 2/1985 | Horrobin . |
| 3,011,949 | 12/1961 | Bilotti .................................. 424/440 |
| 3,882,256 | 5/1975 | De Boer ............................... 424/439 |
| 3,962,416 | 6/1976 | Katzen ................................. 424/439 |
| 4,058,594 | 11/1977 | Williams . |
| 4,097,604 | 6/1978 | Thiele . |
| 4,273,763 | 6/1981 | Horrobin . |
| 4,302,447 | 11/1981 | Horrobin . |
| 4,328,243 | 5/1982 | Horrobin et al. ................. 514/560 |
| 4,370,315 | 1/1983 | Greff et al. ........................ 514/560 |
| 4,386,072 | 5/1983 | Horrobin . |
| 4,393,049 | 7/1983 | Horrobin ............................. 514/560 |
| 4,415,554 | 11/1983 | Horrobin . |
| 4,513,008 | 4/1985 | Revici et al. ....................... 514/560 |
| 4,668,704 | 5/1987 | Hollander et al. ................. 514/560 |
| 4,670,468 | 6/1987 | Hollander et al. ................. 514/560 |

FOREIGN PATENT DOCUMENTS

| | | |
|---|---|---|
| 0037175 | 11/1986 | European Pat. Off. . |
| 0181689 | 10/1987 | European Pat. Off. . |
| 2134782 | 1/1985 | United Kingdom . |

OTHER PUBLICATIONS

Horrobin, D. F., Med. Hypothesis, 6: 469–486 (1980).

*Primary Examiner*—A. Lionel Clingman
*Assistant Examiner*—Willie J. Thompson
*Attorney, Agent, or Firm*—Darby & Darby

[57] ABSTRACT

A composition useful in a method for treating a mammal in order to induce memory enhancement, analgesia, sleep regulation and(or) inhibition of the symptoms of senility, comprises from about 13.0 to about 27.5% by weight of linolenic acid, balance linoleic acid. Physiologically hydrolyzable and pharmacologically acceptable derivatives of these acids may also be used. The specified combination of acids may be administered as pharmaceutical formulations or nutritional compositions.

25 Claims, No Drawings

PHYSIOLOGICALLY ACTIVE AND NUTRITIONAL COMPOSITION

FIELD OF THE INVENTION

The present invention relates to a composition of matter having useful physiological and nutritional activity.

BACKGROUND OF THE INVENTION

It has been recognized for many years that the mammalian body requires for its nutrition relatively large amounts of fats, carbohydrates and proteins, and by contrast relatively small amounts of vitamins and minerals; lack of these latter classes of substances has been held to be accountable for the absence of general good health as well as the incidence of various specific bodily ailments. Vitamins and minerals are normally ingested or otherwise produced from the mammalian diet, but to a certain extent may also or alternatively be produced in the body. For various reasons which may be related to the source of supply or the manufacturing processes used, foods are sometimes lacking or deficient in vitamins and/or minerals, and even where vitamins are synthesized in the body, such a process may not produce the amount required. Over a period of time there has therefore grown up the use of food supplements, or nutritional compositions, to supply the ingredients of this nature required by the body, but which are either not produced therein in sufficient amounts, or are not supplied thereto by the regular diet of the subject in sufficient amounts.

Nutritional compositions are not at the present time, however, restricted merely to a content of vitamins and minerals, as the sole active ingredients. Other materials which are intermediate in metabolic processes and which it is thought may not be produced in sufficient amounts (at least in subjects with abnormal metabolism) may also be present in nutritional compositions. Examples of such other materials are unsaturated fatty acids, such as linoleic acid, gamma-linolenic acid, dihomo-gamma-linolenic acid arachidonic and eicosapentaenoic acids, as well as physiologically compatible derivatives thereof, such as salts, esters and amides of such acids, which may be metabolized in the body to prostaglandins. Prostaglandins are an important group of local hormones which act within the body tissues in which they are synthesized, in roles which are not entirely understood, though they may act at least to lower blood pressure, and to induce smooth muscle to contract.

Horrobin, in Med. Hypotheses 6: 469–486 (1980), has also proposed that a metabolic abnormality in the synthesis of certain prostaglandins is responsible for allowing an initial cancer cell to divide indefinitely, the abnormality being in particular, inhibition of the enzyme delta-6-desaturase which converts essential unsaturated fatty acids in normal cells to prostaglandins. He has also proposed pharmaceutical compositions (see e.g. EP No. 0037175 published Oct. 7, 1981 and prior patent applications referred to therein, the contents of which are to be regarded as incorporated herein by reference) comprising certain unsaturated fatty acids together with other ingredients which enhance formation in the body of essential prostaglandins and therefore bypass the metabolic abnormality referred to above.

In general, fatty acids in combined form are present in animal and vegetable fats and oils, but vegetable oils such as corn, cottonseed and soya oils contain in general a higher ratio of unsaturated to saturated acids, than do animal fats. A higher proportion of polyunsaturated fatty acids (such as linoleic and linolenic acids) in the diet apparently tends to reduce the incidence of heart disease, although whether this is due to a positive effect of the polyunsaturated compounds themselves, rather than to an intake of a correspondingly lower proportion of saturated compounds (and of cholesterol which is also present in animal fats), or to a lower fat intake overall, remains uncertain.

It has now been surprisingly found in accordance with the present invention, that a combination of two naturally occurring polyunsaturated acids within a certain range of proportions, produces certain beneficial effects in the human and animal body, including memory enhancement, analgesia, sleep regulation and inhibition of the symptoms of senility. Experiments carried out by the inventor support the belief that it is the combination of these acids themselves in particular proportions which is the active factor in producing the beneficial effects just referred to; there is no evidence at the present time that such effects are connected with the metabolization of these polyunsaturated acids to other substances.

SUMMARY OF THE INVENTION

The present invention accordingly provides a composition of matter which comprises (a) from about 13.0 to about 27.5% by weight of a compound selected from linolenic acid and derivatives thereof, calculated as the free acid, the derivatives of linolenic acid being both physiologically hydrolyzable and pharmacologically acceptable, and (b) about 87.0 to about 72.5% by weight of a compound selected from linoleic acid and derivatives thereof, calculated as the free acid, the derivatives of linoleic acid being both physiologically hydrolyzable and pharmacologically acceptable.

The present invention also provides, in another aspect, a pharmaceutical formulation which comprises the composition of matter as just defined, together with at least one pharmaceutically acceptable substance selected from diluents, carriers and adjuvants.

In yet another aspect, the invention provides a nutritional composition, adapted for consumption by mammals, characterized by the presence of (i) an orally ingestible diluent or carrier, (ii) at least one compound selected from linolenic acid and physiologically non-deleterious and hydrolyzable derivatives thereof and (iii) at least one compound selected from linoleic acid and physiologically non-deleterious and hydrolyzable derivatives thereof, such that the proportion of ingredient (ii) calculated as a percentage by weight of the combined ingredients (ii) and (iii) is from about 13.0 to about 27.5%, each of (ii) and (iii) being calculated as free acids.

In still another aspect, there is provided by the invention a method for treating a mammal for the purpose of inducing in the mammal a beneficial effect selected from memory enhancement, analgesia, sleep regulation and inhibition of the symptoms of senility which comprises administering to the mammal a composition of matter or a formulation as defined above.

It will be appreciated that the compositions and formulations of the invention are in particular intended for administration to humans, or for human consumption, for the purpose of inducing in them at least one of the aforementioned beneficial effects.

DETAILED DESCRIPTION OF THE INVENTION

The composition of matter according to the invention preferably comprises from about 14.3 to about 25.0% by weight of component (a) and about 85.7 to about 75.0% by weight of component (b), more preferably from about 16.3 to about 24.4% by weight of component (a) and about 83.7 to about 75.6% by weight of component (b).

In accordance with a particular embodiment of the invention, a special memory enhancement effect has been noted when the composition of matter comprises from about 20.0 to about 24.4% by weight of component (a) and about 80.0 to about 75.6% by weight of component (b) or from about 18.2 to about 22.2% by weight of component (a) and about 81.8 to about 77.8% by weight of component (b); and more particularly when the composition comprises either about 22.2% by weight of component (a) and about 77.8% by weight of component (b), or about 20.0% by weight of component (a) and about 80.0% by weight of component (b).

These preferred percentage proportions by weight are also applicable to the relationship between the at least one compound selected from linolenic acid and physiologically non-deleterious and hydrolyzable derivatives thereof, and the at least one compound selected from linoleic acid and physiologically non-deleterious and hydrolyzable derivatives thereof (calculated as the free acids), in the nutritional compositions of the invention.

Since, as has been intimated above, it is believed that the combination of linoleic and linolenic acids is the active principle per se which induces the effects mentioned, it will be appreciated by those skilled in the art that instead of the acids themselves, there may be utilized in the composition of the invention derivatives of these acids which are both physiologically hydrolyzable (to the corresponding acids) and pharmacologically acceptable. Such derivatives may for example be selected from salts, esters and amides of the respective acids.

Among suitable salts there may be mentioned the ammonium, sodium, potassium, calcium and magnesium salts as salts with substituted mono- and di-substituted amines and the analogous saturated heterocyclic compounds containing an NH group in the ring, so long as the amines and the analogues in question are physiologically acceptable. As suitable esters there may be mentioned, for example, the ethyl and glyceryl esters. Amides of the acids may also be utilized, e.g. amides of the acids with substituted mono- and di-substituted amines and with the analogous saturated heterocyclic compounds containing an NH group in the ring, so long as the amines and the analogues in question are physiologically acceptable. It will be appreciated that the latter stipulation is necessary (in the case of the amine salts, the amides and their heterocyclic analogues) since it is to be expected that such derivatives will metabolize in the body to the desired acids and the starting amines or heterocyclic compounds. It will of course be evident to a person skilled in the art how to select a particular salt, ester or amide, so as to comply with the requirements of physiologically hydrolyzing to the corresponding acids, and pharmacological acceptability.

The pharmaceutical formulation provided in accordance with the present invention may be adapted for oral, parenteral or rectal administration, and it may be in the form of dosage units. The diluents, carriers and adjuvants are those conventionally used in pharmaceutical and veterinary formulation.

For oral administration, the pharmaceutical formulations of the invention may be utilized as e.g. tablets, capsules, emulsions, solutions, syrups or suspensions. For parenteral administraton, the formulations may be utilized as ampoules, or otherwise as suspensions, solutions or emulsions in aqueous or oily vehicles. The need for suspending, stabilizing and/or dispersing agents will of course take account of the fact of the solubility or otherwise of the linoleic and linolenic acids, or of their derivatives used in the formulations, in the vehicles which are used in particular embodiments. Thus, for example, where the acids themselves are used, account will be taken of the fact that these have a relatively low water solubility and in general a relatively high oil solubility. The formulations may additionally contain e.g. physiologically compatible preservatives and antioxidants.

The pharmaceutical formulations of the invention may also be utilized as suppositories with conventional suppository bases such as cocoa butter or other glycerides. As is well known in the pharmaceutical art, the formulations may also be made available in a depot form which will release the active composition slowly in the body, over a preselected time period.

The nutritional composition according to the invention includes as a necessary component an orally ingestible diluent or carrier; this may for example comprise a substance selected from sugar-based confectionery, a manufactured cereal, a fruit or vegetable product, a beverage or beverage concentrate, or any inert diluent, carrier or excipient known in the pharmaceutical art. It is intended generally that ingredients (ii) and (iii), as previously defined, may be used in nutritional compositions in any of the forms in which these are known and practised in the art. Thus, the nutritional compositions may take the form of, e.g., sugar-based confectionery such as candies or chocolate, breakfast cereals, fruit or vegetable purees or beverages, other beverages (including those based on carbonated water), or beverage concentrates generally (including those in the form of e.g. powders, granules, flakes or crystals, which are intended to be mixed with hot or cold water and/or milk). The nutritional compositions may also generally be in the form of powders, tablets, capsules, solutions, concentrates, syrups, suspensions, gels or dispersions. It will be evident that when the nutritional compositions take the form of dispersions or suspensions, it will usually be necessary to use an acceptable (i.e. non-toxic and otherwise suitable) dispersing or suspending agent, as is well known in the nutritional and pharmaceutical arts. When these compositions are utilized in the form of capsules, it will be evident that gelatin or other known suitable ingestible materials may be used for encapsulation.

The present invention moreover includes the nutritional compositions described herein, which are adapted for consumption by non-human, as well as human mammals.

The present invention further includes nutritional compositions which also include any of the known vitamins. Thus for example, such compositions (which may be, but need not be, in the form of aqueous suspensions) may comprise at least one watersoluble vitamin selected from thiamine, riboflavin, niacin, pyridoxine, pantothenic acid, biotin, folic acid, cobalamin and ascorbic acid. Alternatively or additionally, such compositions may comprise at least one oil-soluble vitamin selected from retinol, calciferol, tocopherol and menadione. The nutritional compositions of the present invention may also comprise in combined form at least one element selected from sodium, potassium, calcium, phosphorus, magnesium, chlorine and sulfur, and additionally or alternatively, at least one element selected from iron, copper, iodine, manganese, cobalt, zinc, molybdenum, fluorine, selenium and chromium. These compositions may also contain other natural or synthetic antioxidants.

The nutritional compositions of the present invention may also comprise other unsaturated fatty acids, such as for example those known to be metabolized in the body to prostaglandins, e.g. dihomo-gamma-linolenic acid, arachidonic and eicosapentaenoic acids, as well as physiologically compatible derivatives thereof, such as salts, esters and amides of such acids.

The invention will be illustrated by the following Examples.

EXAMPLE I

TREATMENT OF EXPERIMENTAL ANIMALS

METHOD: Subjects were male Long Evans (hooded) rats weighing initially 100 g. They were housed individually in hanging stainless steel, wire-mesh cages in a well-ventilated room at an ambient temperature of 20°-22° C. Light (Vita-Lite, Dura-Test, N.J.) was provided from 06.00 hrs. to 18.00 hrs. daily. A control group of rats (Group A) was fed a diet of linoleic acid 35 mg./kg. diet plus linolenic acid 0.15 mg./kg. diet. Other groups of rats received the same diet, plus a daily aqueous injection of a mixture of linoleic and linolenic acids (with polyethylene glycol emulsifier), each rate receiving by injection 25 mg. linolenic acid, the balance being linoleic acid. (It will be appreciated that the amounts of linoleic and linolenic acids ingested by the rats from the diet just described is insignificant compared with the amounts of these substances administered by injection.) The composition of the injected unsaturated fatty acid mixture was varied among different experimental groups; the percentage by weight of linolenic acid in the mixture was as follows (balance linoleic acid): 25.0; 22.2; 20.0; 18.2; 16.7; 15.4; and 14.3 (these groups were respectively labelled B, C, D, E, F, G and H. Otherwise expressed, the ratios by weight were respectively; 1:3; 1:3.5; 1:4; 1:4.5; 1:5; 1:5.5; and 1:6.0. Another route of administration (i.e., supplemented water or an enriched diet) was tested with closely similar results. Throughout the experiment the rats had free access to food and water. Handling of the rats was kept to a minimum, so as not to interfere with the learning.

Every week groups of rats, from each treatment regimen, were tested in the learning apparatus. The level of motor activity, pain threshold, colonic temperature and d-amphetamine-induced hypothemia were tested in different groups. The order of testing was as follows: first day, motor activity; second day, pain threshold; third day, thermoregulation.

The learning apparatus is known from the scientific literature. Briefly, a circular tank (110 cm. in diameter) was filled with water (at the 40 cm. level), which was made opaque by the addition of powdered milk, so that rats swimming in the tank were unable to see an escape platform (7.5 cm. in diameter) submerged 2 cm. below the water level. Each animal was released facing the wall in one of four predetermined starting points located every 90° around the inner perimeter. A masslearning technique was used, and each rat was tested 8 times per day in the tanks. The order of starting points was randomly predetermined. Each rat was allowed 120 seconds to find the platform, and intertrial interval was 20 seconds. The rats were tested during 3 consecutive days. During this period the platform was in the same location in the tank. After completion of the session on day 3, the platform was removed to another location in the tank, and the performance of rats in the new position was recorded. For each of the 24 trials (8 trials×3 days) the latency to reach the platform was recorded. A cut-off point criterion (i.e., the first trial to reach latency of 10 seconds, without increasing the latency in a later trial) was used to calculate the learning capacity of each diet group. To calculate the resistance to extinction, the time which the rats spent in the "old position" in the first trial was recorded.

The level of motor activity was assessed in an open field apparatus by recording the number of horizontal movements (infrared photobeam crossing) and rearing movements (determined from videotapings) made during the 15 minute sessions. The apparatus was very similar to the one previously described by Coscina et al. in 1986.

Pain threshold was measured with a hot plate (60×60 cm.) heated by a thermostatic bath (Hakke, Germany) to 58+/−0.2° C. The latency to lick the paw was recorded to the nearest 0.1 second. On the third day, the basic colonic temperature of each rat was measured (YSI telethermometer, model 43TA, Yellow Springs, Ohio. The rat was then injected with 15.0 mg./kg., i.p., d-amphetamine and placed immediately into a 4° C. cold room for 1 hour.

All tests were conducted between 10.00 and 14.00 hrs. There were 9 rats in each experimental group. At the end of each week of the experiment, the brain of the rats was removed for biochemical analysis for a different study. All experiments were conducted "double blind," i.e., the experimenter was unaware of the diet fed to the individual subjects or which treatment the rat received. Comparisons across diets and weeks of treatment were analyzed by analysis of variance with contrast tests.

RESULTS:

TABLE 1

| GROUP | NUTRITIONAL FACTORS | |
|---|---|---|
| | FOOD INTAKE(K Cal) | WEIGHT GAIN |
| A | 2565 +/− 39 | 237 +/− 4.7 |
| B | 2575 +/− 80 | 230 +/− 7.0 |
| C | 2545 +/− 75 | 235 +/− 2.8 |
| D | 2534 +/− 68 | 237 +/− 4.6 |
| E | 2543 +/− 72 | 239 +/− 6.1 |
| F | 2562 +/− 57 | 235 +/− 3.3 |
| G | 2586 +/− 48 | 238 +/− 3.9 |
| H | 2533 +/− 61 | 234 +/− 5.5 |
| Data expressed as M +/− SEM | | |
| p | N.S. | N.S. |

Unsaturated fatty acid treatment has no effect on either the amount of food intake (in kCalthe rate of body weight gain.

LEARNING

TABLE 2

NUMBER OF TRIALS TO REACH CRITERION (10 secs.)

| GROUP (P) | WEEKS OF TREATMENT | | | | |
|---|---|---|---|---|---|
| | 0 | 1 | 2 | 3 | 4 |
| A (N.S.) | 19.6 +/− 3.3 | 19.0 +/− 3.7 | 20.3 +/− 2.5 | 18.5 +/− 2.9 | 19.1 +/− 2.7 |
| B (N.S.) | 20.1 +/− 4.1 | 18.0 +/− 4.0 | 19.9 +/− 4.5 | 17.1 +/− 4.0 | 17.0 +/− 3.2 |
| C (0.01) | 17.1 +/− 3.3 | 12.5 +/− 2.1* | 10.7 +/− 4.1* | 7.9 +/− 3.9* | 5.6 +/− 2.5* |
| D (0.001) | 18.5 +/− 2.0 | 9.3 +/− 2.6* | 7.1 +/− 2.9* | 6.1 +/− 2.8* | 6.1 +/− 2.5* |
| E (0.01) | 19.1 +/− 2.3 | 14.2 +/− 3.7* | 12.8 +/− 3.9* | 9.6 +/− 3.0* | 9.0 +/− 3.4* |
| F (0.01) | 19.5 +/− 3.5 | 16.1 +/− 2.6 | 11.2 +/− 1.1* | 9.2 +/− 1.8* | 7.9 +/− 1.0* |
| G (N.S.) | 19.7 +/− 3.8 | 18.1 +/− 3.3 | 18.4 +/− 2.9 | 17.9 +/− 4.1 | 18.6 +/− 2.6 |
| H (N.S.) | 21.0 +/− 4.0 | 20.0 +/− 3.0 | 19.6 +/− 3.1 | 18.8 +/− 3.9 | 19.1 +/− 3.0 |
| P | N.S. | 0.01 | 0.01 | 0.01 | 0.01 |

*Statistically differs from Control (M +/− SEM)

Treatment with the ratios 1:3.5 to 1:5 (Groups C to F) has a significant effect on the rate of learning. The optimal ratio was 1:4 (Group D).

TABLE 3

TIME IN THE 'WRONG' LOCATION; MEANS OF THE FIRST 2 TRIALS

| GROUP (P) | WEEKS OF TREATMENT | | | | |
|---|---|---|---|---|---|
| | 0 | 1 | 2 | 3 | 4 |
| A (N.S.) | 22.9 +/− 3 | 24.3 +/− 4 | 19.0 +/− 3 | 22.3 +/− .4 | 25.1 +/− 4 |
| B (N.S.) | 18.5 +/− 3 | 19.4 +/− 4 | 20.6 +/− 6 | 20.6 +/− 4 | 20.1 +/− .5 |
| C (0.001) | 20.3 +/− 4 | 30.9 +/− 2* | 35.3 +/− 4* | 39.2 +/− 4* | 49.4 +/− 3* |
| D (0.01) | 19.5 +/− 3 | 24.1 +/− 3 | 29.3 +/− 4* | 36.6 +/− 4* | 39.1 +/− 4* |
| E (0.01) | 20.8 +/− 4 | 25.1 +/− 4 | 30.1 +/− 3* | 33.1 +/− 4* | 36.1 +/− 5* |
| F (0.01) | 19.4 +/− 3 | 22.1 +/− 3 | 29.1 +/− 5* | 30.1 +/− 5* | 32.2 +/− 5* |
| G (N.S.) | 22.8 +/− 4 | 19.4 +/− 3 | 19.0 +/− 3 | 19.6 +/− 4 | 18.1 +/− 4 |
| H (N.S.) | 19.1 +/− 5 | 18.7 +/− 5 | 19.9 +/− 4 | 21.1 +/− 3 | 19.6 +/− 5 |
| P | N.S. | 0.01 | 0.001 | 0.001 | 0.001 |

*Statistically differs from Control (M +/− SEM).

Unsaturated fatty acid treatment with ratios of 1:3.5–1:5 (Groups C to F) has a significant effect on retention of the old learning. The most effective ratio was 1:3.5 (Group C).

MOTOR ACTIVITY

TABLE 4

AT THE END OF THE 4 WEEKS' TREATMENT

| GROUP | LINE CROSSING | REARING |
|---|---|---|
| A | 76.0 +/− 27 | 75.0 +/− 5.0 |
| B | 74.0 +/− 30 | 75.5 +/− 5.5 |
| C | 70.7 +/− 25 | 76.0 +/− 4.5 |
| D | 70.3 +/− 33 | 84.3 +/− 5.5 |
| E | 72.1 +/− 29 | 77.7 +/− 6.6 |
| F | 74.4 +/− 32 | 74.6 +/− 5.1 |
| G | 72.5 +/− 25 | 76.9 +/− 6.1 |
| H | 75.5 +/− 31 | 80.0 +/− 5.5 |
| p | N.S. | N.S. |

None of the treatment has any effect on horizontal or on vertical movement.

PAIN THRESHOLD

TABLE 5

| GROUP (P) | WEEKS OF TREATMENT | | | | |
|---|---|---|---|---|---|
| | 0 | 1 | 2 | 3 | 4 |
| A (N.S.) | 7.9 +/− .9 | 7.8 +/− .8 | 8.0 +/− .6 | 7.9 +/− .9 | 8.1 +/− .9 |
| B (N.S.) | 8.0 +/− .8 | 7.9 +/− .7 | 8.0 +/− .9 | 8.1 +/− .7 | 7.8 +/− .7 |
| C (0.01) | 7.8 +/− .6 | 11.9 +/− .7 | 13.9 +/− .7* | 16.5 +/− .6* | 20.1 +/− 1.1* |
| D (0.01) | 8.1 +/− .8 | 12.1 +/− .6* | 14.5 +/− .6* | 18.2 +/− .7* | 21.1 +/− .9* |
| E (0.01) | 7.8 +/− .6 | 9.0 +/− .9* | 9.0 +/− .8* | 14.1 +/− .7* | 17.4 +/− .7* |
| F (0.01) | 8.1 +/− .9 | 9.9 +/− .9 | 11.5 +/− .7 | 14.1 +/− .7* | 16.3 +/− .7* |
| G (N.S.) | 7.6 +/− .7 | 8.0 +/− .3 | 8.8 +/− .8 | 8.0 +/− .8 | 8.1 +/− .9 |
| H (N.S.) | 8.0 +/− .9 | 8.0 +/− .4 | 8.5 +/− .5 | 8.3 +/− .7 | 8.3 +/− .7 |
| P | N.S. | 0.05 | 0.01 | 0.01 | 0.01 |

*Statistically differs from control (M +/− SEM).

Unsaturated fatty acid treatments with ratios of 1:3.5 to 1:4.5 (Groups C to E) cause analgesia among rats which were placed on a hot plate (58° C.). The most effective ratio seems to be 1:4 (Group D).

THERMAL RESPONSE TO D-AMPHETAMINE AT 4° C.

TABLE 6

| GROUP (P) | WEEKS OF TREATMENT | | | | |
|---|---|---|---|---|---|
| | 0 | 1 | 2 | 3 | 4 |
| A (N.S.) | −1.9 +/− .7 | −1.8 +/− .8 | −1.7 +/− .6 | −1.9 +/− .7 | −2.0 +/− .9 |
| B (N.S.) | −1.9 +/− .9 | −1.9 +/− .9 | −1.8 +/− .7 | −2.0 +/− .9 | −2.1 +/− .7 |
| C (0.001) | −2.0 +/− .5 | −.9 +/− .3* | −.8 +/− .3* | +.9 +/− .9* | +1.1 +/− .7* |
| D (0.001) | −2.0 +/− .7 | −.9 +/− .6* | +.9 +/− .5* | +1.1 +/− .7* | +1.2 +/− .6* |
| E (0.001) | −1.9 +/− .8 | −.6 +/− .9* | +.6 +/− .3* | +.9 +/− .9* | +.9 +/− .9* |

TABLE 6-continued

| GROUP (P) | WEEKS OF TREATMENT | | | | |
|---|---|---|---|---|---|
| | 0 | 1 | 2 | 3 | 4 |
| F (0.01) | −1.9 +/− .8 | −.9 +/− .7* | −.9 +/− .7* | +.7 +/− .5* | +1.1 +/− .9* |
| G (N.S.) | −1.9 +/− .9 | −2.0 +/− .7 | −1.8 +/− .7 | −1.8 +/− 1.2 | −1.9 +/− .7 |
| H (N.S.) | −2.0 +/− .9 | −1.9 +/− .7 | −2.1 +/− .9 | −2.0 +/− .9 | −2.2 +/− 1.1. |
| P | N.S. | 0.05 | 0.01 | 0.01 | 0.01 |

*Statistically differs from Control (M +/− SEM)

Unsaturated fatty acid treatment protected rats from d-amphetamine induced hypothermia at ambient temperature of 4° C. A ratio of 1:4 (Group D) seems to be most effective.

SLEEP PARAMETERS

A small number of rats (n=6) received unsaturated fatty acids at a ratio of 1:3.5 (as in Group C) for 4 weeks. At the end of the treatment period the length of total sleeping hours and REM percentage was examined and compared with saline treated rats. A strong tendency (but not statistically significant) of longer sleeping hours (+30%) and an increase in REM periods (+18%) were found in treated rats.

THE EFFECT OF IRON DEFICIENCY ON LEARNING

Iron deficiency induced severe learning deficits both in water maze and in water tank learning. Similar deficits were obtained by brain lesions. While control rats needed 19.6+/−3.3 trial to reach the criterion of learning, iron-deficient rats needed 26.4+/−1.1 to reach the same performance. Iron-deficient rats treated for 3 weeks with 1:4 ratio (as in Group D) before training reached the criterion in 15.9+/−4.8 trial while saline treated rats had the same 27.0+/−1.2 trials to criterion.

THE EFFECT OF AGING ON LEARNING

Old male rats (20-22 months old) showed a strong deficit in learning. Among 7 non-treated rats none was able to learn the swim test. The group of old rats (n=6) was able to learn the swim test after 1:4 ratio treatment (as in Group D) of 6 weeks duration. They learned the task in 15.9+/−6.1 trials. However, due to the small number of rats, and because it is one trial without replication, it is difficult to draw positive conclusions on the effect of such treatment on old age learning deficit.

EXAMPLE II

STUDY OF HUMANS 225 mg. of the composition of one embodiment of the present invention which contained 22.2% by weight linolenic acid and the balance linoleic acid, was given twice daily to 12 demented geriatric patients (male and female, means age 76.5+/−2). A comparable group of 12 geriatric patients (similar in age and severity of dementia) was given a placebo (lemonade syrup, the vehicle of the unsaturated fatty acid mixture). The treatment length was 28 days. The study was carried out in double-blind fashion; (however, there were some differences between the treatment and the lemonade, mainly in color). The medical staff, doctors and nurses, were instructed to follow the 24 subjects and to tell by the end of the period which one was "improved" on a subjective scale. The medical staff identified correctly 10 of the 12 treated patients as improved, and none of the 11 placebo group (one of the subjects in this group had to leave the experiment because of other medical problems). The patients seemed to be improved in the following aspects: they are more cooperative; they were in a better mood; appetites improved; they were able to remember their way around the hospital, and complained less about sleep disturbances. The food intake (amount and type of food) was not controlled. However, the rate of success in identifying treated subjects was highly significant.

While the present invention has been particularly described with reference to certain embodiments, it will be apparent to those skilled in the art that many modifications and variations may be made. The invention is accordingly not to be construed as limited in any way by such embodiments, rather it is to be defined only by the claims which follow.

I claim:

1. A composition of matter which comprises (a) from about 13.0 to about 27.5% by weight of at least one compound selected from the group consisting of linolenic acid and derivatives thereof, calculated as the free acid, said derivatives of linolenic acid being both physiologically hydrolyzable and pharmacologically acceptable, and (b) about 87.0 to about 72.5% by weight of at least one compound selected from the group consisting of linoleic acid and derivatives thereof, calculated as the free acid, said derivatives of linoleic acid being both physiologically hydrolyzable and pharmacologically acceptable.

2. A composition of matter according to claim 1, which comprises from 14.3 to 25.0% by weight of component (a), balance to make 100% component (b)..

3. A composition of matter according to claim 2, which comprises substantially 20.0% by weight of component (a), balance to make 100% component (b).

4. A composition of matter according to claim 1, which comprises from 20.0 to 24.4% by weight of component (a), balance to make 100% component (b).

5. A composition of matter according to claim 1, wherein said derivatives of linolenic acid and said derivatives of linoleic acid are each selected from the group consisting of salts, esters and amides of the respective acids.

6. A pharmaceutical formulation which comprises:
a composition of matter comprising (a) from 13.0 to 27.5% by weight of at least one compound selected from the group consisting of linolenic acid and derivatives thereof, calculated as the free acid, said derivatives of linolenic acid being both physiologically hydrolyzable and pharmacologically acceptable, and (b) 87.0 to 72.5% by weight of at least one compound selected from the group consisting of linoleic acid and derivatives thereof, calculated as the free acid, said derivatives of linoleic acid being both physiologically hydrolyzable and pharmacologically acceptable, in combination with
at least one pharmaceutically acceptable substance selected from the group consisting of diluents, carriers and adjuvants.

7. A pharmaceutical formulation according to claim 6, and which is adapted for oral, parenteral or rectal administration.

8. A pharmaceutical formulation according to claim 7, which is in the form of dosage units.

9. A pharmaceutical formulation according to claim 6, which is in depot form which will release the active composition slowly in the body, over a preselected time period.

10. A method for treating a mammal for the purpose of inducing therein at least one physiological effect selected from memory enhancement, analgesia, sleep regulation and inhibition of the symptoms of senility, which comprises administering to the mammal a composition according to claim 1.

11. A method for treating a mammal for the purpose of inducing therein at least one physiological effect selected from memory enhancement, analgesia, sleep regulation and inhibition of the symptoms of senility, which comprises administering to the mammal a formulation according to claim 6.

12. A nutritional composition, adapted for consumption by mammals, which is characterized by the presence of (i) an orally ingestible diluent or carrier, (ii) at least one compound selected from the group consisting of linolenic acid and physiologically non-deleterious and hydrolyzable derivatives thereof and (iii) at least one compound selected from the group consisting of selected from linoleic acid and physiologically non-deleterious and hydrolyzable derivatives thereof, such that the proportion of ingredient (ii) calculated as a percentage by weight of the combined ingredients (ii) and (iii) is within the range of from about 13.0 to about 27.5%, each of (ii) and (iii) being calculated as free acids.

13. A nutritional composition according to claim 12 and wherein said proportion is from 14.3 to 25.0%.

14. A nutritional composition according to claim 13, wherein said proportion is substantially 20.0%.

15. A nutritional composition according to claim 12 and wherein said proportion is from 20.0 to 24.4%.

16. A nutritional composition according to claim 12, wherein said derivatives of linolenic acid and said derivatives of linoleic acid are each selected from the group consisting of salts, esters and amides of the respective acids.

17. A nutritional composition according to claim 12, wherein said orally ingestible diluent or carrier comprises a substance selected from the group consisting of sugar-based confectionery, a manufactured cereal, a fruit or vegetable product, a beverage or beverage concentrate, a ground meat product or a vegetable analogue thereof, or any inert diluent, carrier or excipient known in the pharmaceutical art.

18. A nutritional composition according to claim 12, which comprises at least one additional ingredient selected from the group consisting of a) the water-soluble vitamins thiamine, riboflavin, niacin, pyridoxine, pantothenic acid, biotin, folic acid, cobalamin and ascorbic acid, ($\beta$) the oil-soluble vitamins retinol, tocopherol, caliciferol, tocopherol and menadione, ($\tau$) in combined form the elements sodium, potassium, calcium, phosphorus, magnesium, chlorine and sulfur, iron, copper, iodine, manganese, cobalt, zinc, molybdenum, fluorine, selenium and chromium, ($\delta$) unsaturated fatty acids which are known to be metabolized in the body to prostaglandins, and physiologically compatible derivatives (such as salts, esters and amides) of said fatty acids, and ($\epsilon$) acceptable antioxidants, dispersing and suspending agents, and water.

19. A nutritional composition according to claim 12, which is in the form of a powder, tablet, capsule, solution, concentrate, syrup, suspension, gel or dispersion.

20. A composition of matter according to claim 2, which comprises from 16.3 to 24.4% by weight of component (a), balance to make 100% component (b).

21. A composition of matter according to claim 20, which comprises from 18.2 to 22.2% by weight of component (a), balance to make 100% component (b).

22. A composition of matter according to claim 4, which comprises substantially 22.2% by weight of component (a), balance to make 100% component (b).

23. A nutritional composition according to claim 13 and wherein said proportion is from 16.3 to 24.4%.

24. A nutritional composition according to claim 23 and wherein said proportion is from 18.2 to 22.2%.

25. A nutritional composition according to claim 15 and wherein said proportion is substantially about 22.2%.

* * * * *